(12) United States Patent
Moy et al.

(10) Patent No.: US 8,872,132 B2
(45) Date of Patent: *Oct. 28, 2014

(54) SYSTEM OF FLUORESCENCE ANALYSIS OF A FIELD IN AN ILLUMINATED AREA

(71) Applicant: Commissariat a l'Energie Atomique, Paris (FR)

(72) Inventors: Jean-Pierre Moy, Saint Egreve (FR); Philippe Rizo, La Tronche (FR); Anabella Da Silva, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/067,457

(22) Filed: Oct. 30, 2013

(65) Prior Publication Data

US 2014/0055605 A1 Feb. 27, 2014

Related U.S. Application Data

(63) Continuation of application No. 12/331,925, filed on Dec. 10, 2008, now Pat. No. 8,598,540.

(51) Int. Cl.
*G01J 1/58* (2006.01)
*A61B 1/06* (2006.01)
*A61B 5/00* (2006.01)
*A61B 1/04* (2006.01)
*G01N 21/64* (2006.01)

(52) U.S. Cl.
CPC .............. *G01N 21/64* (2013.01); *A61B 1/0684* (2013.01); *A61B 5/0059* (2013.01); *G01N 2021/6441* (2013.01); *G01N 21/6456* (2013.01); *G01N 2021/6419* (2013.01); *A61B 5/0071* (2013.01); *A61B 1/043* (2013.01); *A61B 5/444* (2013.01); *A61B 1/0638* (2013.01)
USPC ...................... 250/458.1; 250/459.1; 359/385; 600/309

(58) Field of Classification Search
USPC ............. 250/458.1, 459.1; 359/385; 600/160, 600/309, 310, 317, 476, 477
See application file for complete search history.

(56) References Cited

U.S. PATENT DOCUMENTS 8,598,540 B2 * 12/2013 Moy et al. .................. 250/458.1

* cited by examiner

*Primary Examiner* — Walter L Lindsay, Jr.
*Assistant Examiner* — Jessica L Eley
(74) *Attorney, Agent, or Firm* — Vedder Price PC

(57) ABSTRACT

A system of analysis with the naked eye and by fluorescence of a field in an illuminated area comprising a periodically-excited first low-remanence white light illumination source; a second light source for exciting fluorescent elements located in said field, active at least during part of the time periods when the first source is off; and a fluorescence analysis device active during time periods when the first source is off and the second source is on.

7 Claims, 2 Drawing Sheets

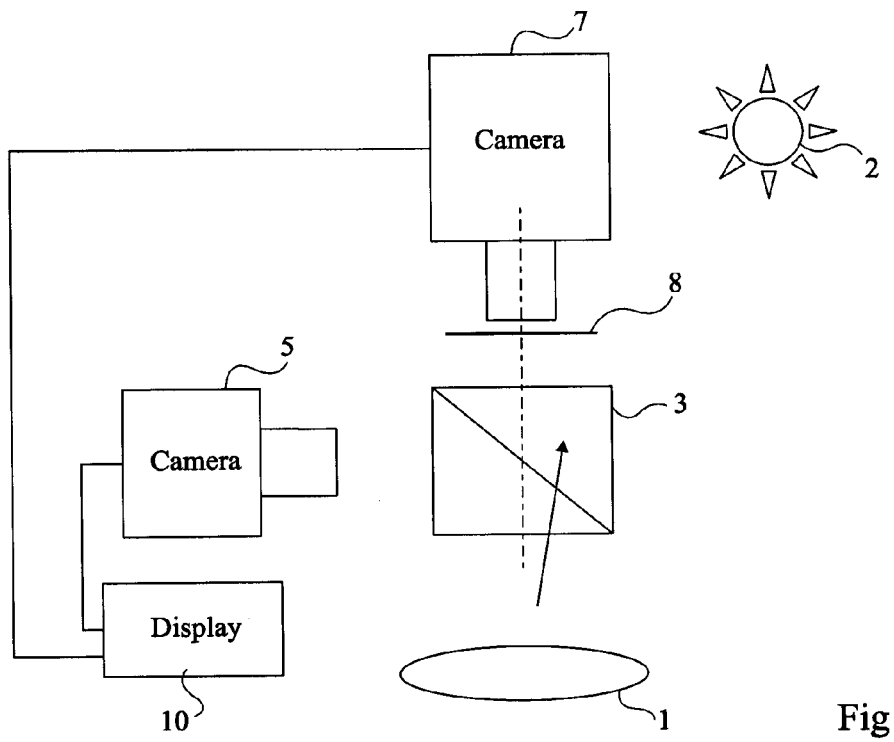
Fig 1 "Prior Art"
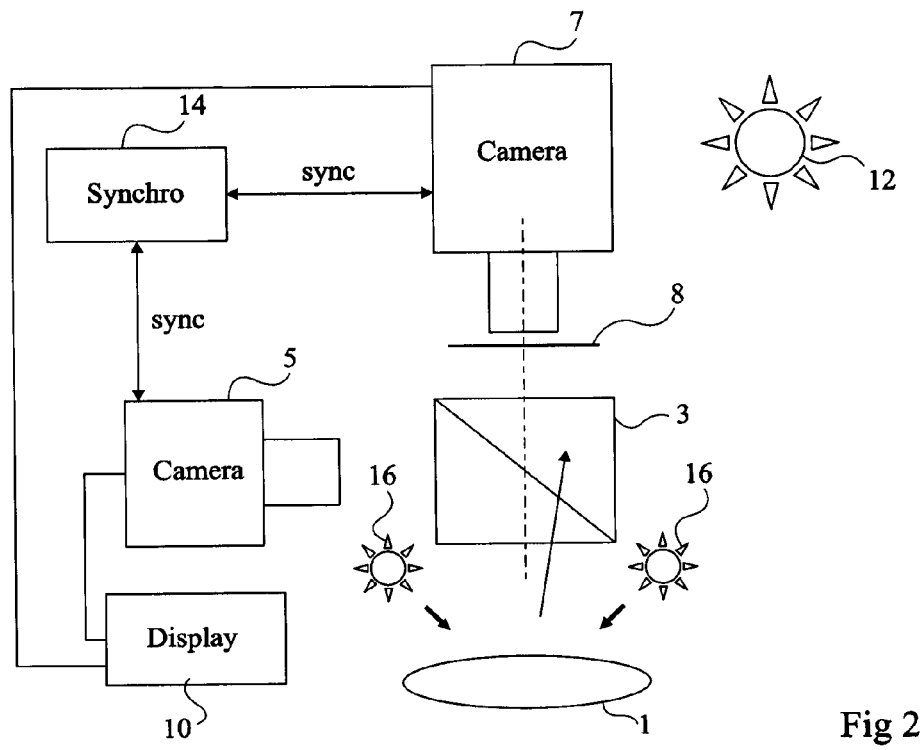
Fig 2

SYSTEM OF FLUORESCENCE ANALYSIS OF A FIELD IN AN ILLUMINATED AREA

CROSS-REFERENCE TO RELATED APPLICATION

The instant application is a continuation of co-pending U.S. patent application Ser. No. 12/331,925 filed on Dec. 10, 2008 and entitled "System Of Fluorescence Analysis Of A Field In An Illuminated Area", the teachings of which are incorporated herein by this reference.

FIELD

The present invention relates to the analysis in an observation field of the radiation of fluorescent elements, the observation field being arranged in an illuminated area so that this field and the surrounding areas can also be directly observed in a natural fashion.

BACKGROUND

The state of the art and the present invention will essentially be discussed hereafter in the context of a medical or veterinary application of the present invention, where the illuminated area is an operating room or another medical or veterinary intervention room, for example, a dermatological intervention room. The observation field or operation area then is a portion of a patient's body, with locations which have fixed fluorescent elements indicative of specific physiological characteristics. For example, on the skin, areas affected by disease or attacked by parasites are likely to fix more fluorescent elements than other skin areas. Then, an observation of the fluorescent elements (or markers) can reveal these areas. Similarly, in an operation area, a failing portion of an organ, for example, cancerous cells, is likely to specifically fix fluorescent elements. In both cases, the patient and the room in which he is must be illuminated so that the practitioner can observe the diseased area and possibly intervene, and the fluorescence light must also be observed. More specifically, in an operating room where a surgeon must operate, it is important for the operation area to be particularly well illuminated.

A problem which arises for the analysis of fluorescent areas is that, generally, the fluorescence light intensity is very low as compared with the normal ambient lighting. In the fluorescence wavelength range of a specific fluorescent element, the fluorescence light often has an intensity from 106 to 107 times lower than the ambient light in the concerned spectral range. It should be noted that this problem of an intensity difference between the white light intended to illuminate the scene to provide a good visibility to the naked eye, and the fluorescence light observed by a camera, does not arise in situations where a white light image and a fluorescence image are both observed by cameras. In such situations, for example, in endoscopy, the intensity of the image resulting from a white light illumination is preferably of the same order of magnitude as the intensity of the fluorescence image.

For operating rooms, in prior art, it has been provided to suppress by filtering in the ambient light the spectrum portion in which the fluorescent elements emit and to detect the fluorescence image with a camera provided with a filter which excludes any light outside the fluorescence spectral band. This method has many disadvantages. The filter must have outstanding performances in terms of extinction, since the ambient light-to-fluorescence ratio is huge (>106); the filtered lighting severely disturbs the colors perception; and each type of fluorescent element imposes a set of filters on the illumination system.

SUMMARY

An object of the present invention is to provide a system for observing fluorescence light in the presence of an ambient illumination which overcomes at least some of the disadvantages of prior systems.

An object of an embodiment of the present invention is to enable to use of an ambient illumination which can be optimized in terms of intensity and of spectral characteristics, independently from the fluorescence analysis.

An object of an embodiment of the present invention is to provide a system which avoids the use of expensive filterings.

An object of an embodiment of the present invention is to provide a system which enables to freely select fluorescent elements having optical characteristics that may be very different.

To achieve these objects, an embodiment of the present invention provides a system of analysis with the naked eye and by fluorescence of a field in an illuminated area comprising a first low-remanence white light illumination source formed of an assembly of light-emitting diodes periodically excited at a frequency greater than 24 Hz; a second light source for exciting fluorescent elements located in said field, active at least during part of the time periods when the first source is off; and a fluorescence analysis device active during time periods when the first source is off and the second source is on.

According to an embodiment of the present invention, the periodic excitation frequency is on the order of 100 Hz.

According to an embodiment of the present invention, the second light source provides light in a spectral region which does not cover the emission spectrum of the fluorescent elements.

According to an embodiment of the present invention, the analysis device is an electronic camera.

According to an embodiment of the present invention, the electronic camera comprises a line-transfer pixel array.

According to an embodiment of the present invention, the image of the electronic camera is superposed to the image provided by another electronic camera observing said field by the light of the first illumination light source.

According to an embodiment of the present invention, the system comprises a third light source having a spectrum substantially complementary to that of the second light source, substantially illuminating the same field, and which is active complementarily to the second light source.

The foregoing objects, features, and advantages of the present invention will be discussed in detail in the following non-limiting description of specific embodiments in connection with the accompanying drawings.

BRIEF DESCRIPTION OF THE DRAWINGS

The features described in this disclosure are set forth with particularity in the appended claims. These features will become apparent from consideration of the following detailed description, taken in conjunction with the accompanying drawings. One or more embodiments are now described, by way of example only, with reference to the accompanying drawings wherein like reference numerals represent like elements and in which:

FIG. 1 shows a system of observation of the fluorescence in an observation field;

FIG. 2 shows a system of observation of the fluorescence in an observation field according to an embodiment of the present invention;

DETAILED DESCRIPTION OF THE PRESENT EMBODIMENTS

Figure 3:
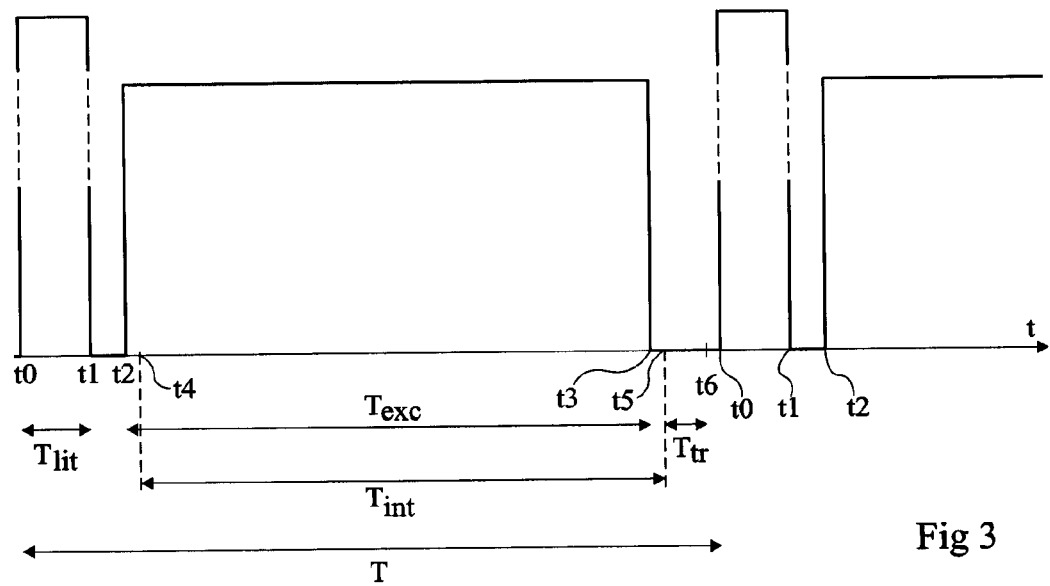
FIG. 3 is a timing diagram intended to explain an operating mode of a system according to an embodiment of the present invention.

FIG. 1 shows an area to be observed or operation area 1 arranged in an operating room illuminated by an ambient illumination source 2, generally a white light source formed of an assembly of incandescent lamps. The operation field is observed with the help of a beam splitter 3, on the one hand, by an optional color camera 5, and on the other hand by a camera 7 sensitive to the sole fluorescence light of operation area 1. This fluorescence light for example results from an illumination by a specific light source, not shown. A filter 8 isolates the spectral range in which the fluorescence light is emitted. Preferably, the images of cameras 5 and 7 are superposed by processing means on a display screen 10 which shows, on the one hand, the entire operation area, and on the other hand the regions of this area more specifically rich in fluorescent elements, these regions being for example marked with a specific color or with specific symbols. Thus, a surgeon which observes the scene with the naked eye can further immediately spot "diseased" areas on display 10 and can thus treat them or eliminate them. This type of installation comes up against the previously-mentioned problems.

FIG. 2 shows a system according to an embodiment of the present invention intended, like the system of FIG. 1, to provide on a display screen 10 the combined image of a color camera 5 of normal observation of an operation area and of a camera 7 sensitive to fluorescence, possibly preceded by a filter 8 corresponding to the emission range of the fluorescent elements. The two cameras simultaneously observe operation area 1 with the help of a beam splitter 3.

In the system of FIG. 2, the ambient illumination light source is a light source 12 which, unlike an incandescent lamp, has a very low remanence, that is, as soon as its supply is stopped (or becomes lower than a given threshold), the generated illumination drops to a null value very quickly, for example, within a few microseconds. An example of a low-remanence white light source is an assembly of single-color light-emitting diodes (LED).

It will be noted that LED white-light sources are generally not of a low remanence. Indeed, LED white-light sources, so-called white LEDs, generally comprise a color LED, for example blue or violet, and one or more phosphors external to the LED, having an emission spectrum that is mixed with the emission spectrum of the LED to produce light having a spectrum generally comprised between 400 nm and at least 700 nm. A white light is accordingly obtained. A drawback of such white LEDs combining an LED and a phosphor is that the remanence of the phosphor is large. While the decrease in the light intensity of the light from the LED when deactivated is fast, lower than 1 µs, the decrease in the light intensity of the light produced by the phosphor is much slower, and generally non-exponential. Thus, the time duration for emissions of the phosphor to become lower than $10^{-6}$ of the maximum emission can be very long, greater than tens of milliseconds. Thus, such LEDs are not low-remanence light sources.

A low-remanence color LED may be supplied by periodic pulses, and it often has the best light output under such conditions. Thus, to illuminate an operating room, a large number of diodes of different colors may be used, their combination enabling to provide light of settable shade (color), particularly adapted to provide good observation, while having a very low remanence time.

The operation of fluorescence-sensitive camera 7 is synchronized by a synchronization device 14 which sets the frequency of the start-up pulses provided to light source 12. Synchronization device 14 activates camera 7, and possibly observation camera 5, only for selected time periods, which will be explained hereafter. An additional light source 16 illuminates operation area 1. Light source 16 also has an operation synchronized by device 14 and enables illuminating the operation area at an optimal excitation wavelength for a specific used fluorescent element. Light source 16 is formed of a plurality of elementary sources, for example, light-emitting diodes or laser diodes, which may be associated with an optical filter enabling to eliminate the wavelengths corresponding to the desired fluorescence. If the fluorescent element is fluorescein, an excitation light having a wavelength close to 488 nm (in blue light) will be used, the fluorescence then being at a wavelength close to 550 nm (in green light). If the fluorescent element is Alexa 750, the excitation light will have a wavelength close to 690 nm (in far red light), the fluorescence then being at a wavelength close to 750 nm (in close infrared light).

The operation of the system of FIG. 2 will be explained in relation with FIG. 3. FIG. 3 shows time t in abscissas and light intensities in ordinates. In the following, it is assumed that the different described phenomena occur with a periodicity T. This periodicity is selected so that, due to the retinal persistence phenomenon, the person observing white light flashes has the feeling of a continuous illumination. The illumination rate will be greater than 24/s, preferably on the order of 100/s.

The low-remanence ambient illumination light source 12 is on during time period $T_{lit}$ between times t0 and t1. The duty cycle is relatively low, that is, if, for example, period T is on the order of 10 milliseconds (100-Hz frequency), the lighting will preferably last for no longer than from 1 to 2 ms. At end t1 of the illumination pulse, the light intensity is assumed to drop very fast, within a time period not visible in the drawing with respect to the illumination time, for example, from 1 to 3 µs.

Between end-of-lighting time t1 and the next start-of-lighting time t0 of the low-remanence light source providing the ambient light, the fluorescence of the illuminated area is analyzed. Thus, for an excitation time period $T_{exc}$ between times t2 and t3, the field to be observed is illuminated by means of light source 16 and, during this time period or for a time period $T_{int}$ shifted by a few microseconds, the light received by camera 7 is integrated. It should be noted that it is important for the integration to end before the beginning of the next illumination but that, however, it is not essential to interrupt the excitation light. Said light may be continuous. As indicated above, each period T comprises a lighting time $T_{lit}$ of the light source shorter than the duration Tint during which the fluorescent light is collected. Thus, if the period T is about 10 ms, the duration $T_{lit}$ can be lower than 2 ms and the duration $T_{int}$ can be greater than 6 ms.

Then, between end-of-integration time t5 and a time t6, for a time period $T_{tr}$, the data collected by the camera are transferred to a memory.

If the intensity of the fluorescence is particularly low, several integration periods $T_{int}$ and several successive transfers may be needed before obtaining an observable image. This is perfectly compatible with the described system.

Thus, according to the described embodiment, it is provided to dissociate ambient illumination periods from fluorescence analysis periods.

Light-emitting diodes or other low-remanence light sources excitable with periodic pulses providing the ambient illumination will be selected by a sufficient number and with sufficient powers to be able to satisfactorily illuminate an operating room and more specifically an operation area even if they are excited by pulses with duty cycles on the order of from 1 to 2/10.

Alternatively, instead of providing specific excitation sources 16 to excite the fluorescent elements, it may be provided for these sources to be formed of part of the light-emitting diodes illuminating the operating room.

Figure 4:
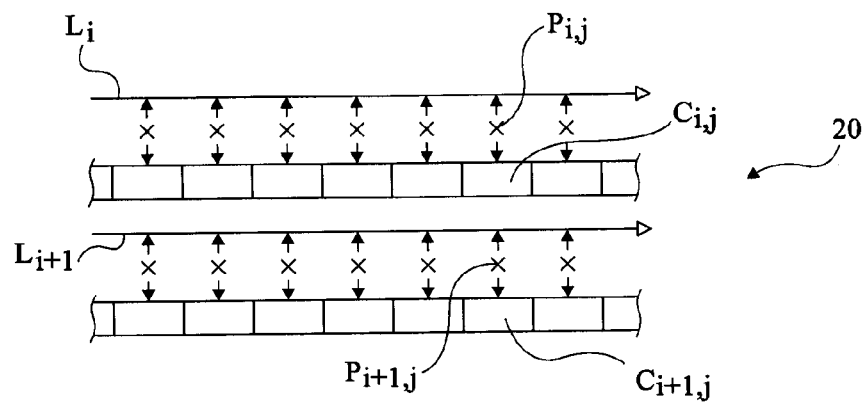
FIG. 4 schematically shows a portion of a pixel array usable according to an embodiment of the present invention.

FIG. 4 illustrates an embodiment of a portion of an image sensor 20 likely to be integrated to fluorescence-sensitive camera 7. In this drawing, pixels $P_{i,j}$, $P_{i+1,j}$ have been shown by crosses. Pixels $P_{i,j}$ correspond to part of the pixels of a line of an array image sensor, and pixels $P_{i+1,j}$ correspond to the pixels of an adjacent line of the same image sensor. Each pixel $P_{i,j}$ can be connected by a first switch to a discharge line $L_j$, symbolized by a connection to a reference voltage. A second switch enables to connect each pixel $P_{i,j}$ to a respective memory cell $C_i$. In a usual embodiment, the transfers are performed by pixel line. Before each integration period $T_{int}$ (time t4 of FIG. 3), all pixels will be connected to the discharge lines to be emptied of the charges created by the illumination. Preferably, the connection between pixels and discharge lines is maintained for the entire time period $T_{lit}$. After this only will the incident fluorescence light intensity enable the building-up of charges at the level of each of the pixels according to the fluorescence light received by this pixel and, at the end of each period, will the data stored in each pixel line be discharged to memory cell lines $C_i$, $C_{i+1}$. This embodiment is particularly simple. It is possible to accumulate charges collected during a large number of periods $T_{int}$, for example 5 to 10 periods $T_{int}$, before reading the array imager and transferring the image to the processing and display means 10. This implementation makes it possible to accumulate the fluorescent signal while reducing the relative read noise. In this implementation, the imager can be a CCD array with interline transfer such as the device CCD KAI 340 manufactured by Kodak or the CCD array 340 manufactured by Sony.

Many other implementations will be possible, provided to provide an image sensor likely to acquire an image or an image portion after the end of an illumination pulse and to transfer this image to a memory before the beginning of the next illumination pulse.

A mechanical shutter or a liquid crystal shutter which periodically obscures the fluorescence image sensor during white light pulses may also be provided. The image sensor can then be a CCD or CMOS sensor. Thus, the accumulation of the fluorescent light will be increased on the sensor, its time duration being for example equal to 5 to 10 periods $T_{int}$, before being transferred to the processing display and means 10.

In the case where the central wavelength of excitation source 16 of the fluorescent elements is in the visible field, the light provided by this source is integrated by the observer's eye during each period with the light of ambient light source 12. As a result, the area illuminated by fluorescence excitation source 16 may appear with a color and/or a contrast different in natural observation from the other areas of the room or other premises containing the observation field. According to a variation of the present invention, to compensate for this effect, excitation sources 16 may be provided to actually be double sources and to comprise, on the one hand, sources such as those described previously capable of exciting the fluorescent elements between periods of illumination with the ambient light, and on the other hand light sources complementary in terms of spectrum to the excitation sources. The complementary sources are excited for at least part of the time period during which the excitation light sources are off outside of periods $T_{exc}$, $T_{int}$, and $T_{tr}$. These complementary sources are excited with a sufficient intensity to have, due to retinal persistence, by eye integration, the resulting light correspond to the ambient light or to a color selected for the observation field.

The present invention is likely to have many other variations which will occur to those skilled in the art. In particular, any light source excitable with pulses and having a very low remanence may be used for the ambient light.

It should be reminded that the present invention, although it has been described in the context of an operating room, generally applies to any system in which it is desired, on the one hand, to observe objects with the naked eye under "natural" light and, on the other hand, to observe with a camera the fluorescence light likely to be provided by areas of the considered objects.

It should also be noted by those skilled in the art that it may be provided for observation field 1 to be likely to contain several fluorescent elements of different characteristics. It may then be provided to analyze the observation field with several cameras, each of which is sensitive to the light of one of the fluorescent elements. In this case, according to the distance between the spectral fluorescence areas of the different fluorescent elements, simultaneous or successive analyzes of the fluorescent elements with the various cameras may be performed.

In the above-described embodiments, it has been provided to display a "natural" image superposed to a fluorescence image. For this purpose, several cameras may aim at the same observation field without using a beam splitter. In certain cases, those skilled in the art may display the fluorescence image only, and not the natural image. Further, the fluorescence image may be superposed to a fixed image, for example, a drawing or a radiography. It may also be provided for the same camera to alternately detect the natural image and the fluorescence image.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. A system of analysis with the naked eye and by fluorescence of a field in an illuminated area comprising:
   a first low-remanence white light illumination source formed of an assembly of single-color light-emitting diodes periodically excited at a frequency greater than 24 Hz to provide ambient light;
   a second light source for exciting fluorescent elements located in said field by emitting an excitation light within the visible range, active at least during part of the time periods when the first source is off, the lighting periods of the first light source being shorter than the lighting periods of the second light source;
   a fluorescence analysis device active during time periods when the first source is off and the second source is on, wherein the spectrum of the ambient light is complementary to that of the excitation light such that the resultant color of light on the field, as perceived by the naked eye, is the color of the ambient light or a color selected for observation of the field, wherein the analysis device is an electronic camera comprising a pixel array, the data collected by the pixels being transferred to a memory at the excitation frequency of the first source; and a liquid crystal shutter for periodically obscuring the fluorescence analysis device when the first light source is on.

2. The system of claim 1, wherein said periodic excitation frequency is on the order of 100 Hz.

3. The system of claim 1, wherein the duty cycle of the on-state of the first light source is low.

4. The system of claim 1, wherein the image of the electronic camera is superposed to the image provided by another electronic camera observing said field by the light of the first illumination light source.

5. A system of analysis with the naked eye and by fluorescence of a field in an illuminated area comprising:

a first low-remanence white light illumination source formed of an assembly of single-color light-emitting diodes periodically excited at a frequency greater than 24 Hz to provide ambient light;

a second light source for exciting fluorescent elements located in said field by emitting an excitation light within the visible range, active at least during part of the time periods when the first source is off, the lighting periods of the first light source being shorter than the lighting periods of the second light source;

a third light source for emitting light having a spectrum substantially complementary to that of the excitation light, substantially illuminating the same filed, active at least during part of the time periods when the excitation light is off, such that the resultant color of light on the field, as perceived by the naked eye, is the color of the ambient light or a color selected for observation of the field;

a fluorescence analysis device active during time periods when the first source is off and the second source is on, wherein the analysis device is an electronic camera comprising a pixel array, the data collected by the pixels being transferred to a memory at the excitation frequency of the first source; and a liquid crystal shutter for periodically obscuring the fluorescence analysis device when the first light source is on.

6. The system of claim 5, wherein the second light source and the third light source are part of a double light source.

7. A system of analysis with the naked eye and by fluorescence of a field in an illuminated area comprising:

a first low-remanence white light illumination source formed of an assembly of single-color light-emitting diodes periodically excited at a frequency greater than 24 Hz;

a second light source for exciting fluorescent elements located in said field by emitting an excitation light within the visible range, wherein the excitation light is continuously on;

a fluorescence analysis device active during time periods when the first source is off, wherein the analysis device is an electronic camera comprising a pixel array, the data collected by the pixels being transferred to a memory at the excitation frequency of the first source; and a liquid crystal shutter for periodically obscuring the fluorescence analysis device when the first light source is on.

* * * * *